United States Patent [19]

Columbus

[11] Patent Number: 5,230,864
[45] Date of Patent: Jul. 27, 1993

[54] GRAVITY ASSISTED COLLECTION DEVICE

[75] Inventor: Richard L. Columbus, Rochester, N.Y.

[73] Assignee: Eastman Kodak Company, Rochester, N.Y.

[21] Appl. No.: 683,385

[22] Filed: Apr. 10, 1991

[51] Int. Cl.$^5$ ............................................. B01L 3/02
[52] U.S. Cl. ....................................... 422/100; 422/72; 422/73; 422/102; 73/864.02; 128/763; 128/766; 128/767
[58] Field of Search ......................... 422/61, 58, 72-73, 422/100, 102; 128/760, 763-767; 73/864-864.02, 864.11; 436/63

[56] References Cited

U.S. PATENT DOCUMENTS

| | | | |
|---|---|---|---|
| 2,726,549 | 12/1955 | Geffen . | |
| 2,737,812 | 3/1956 | Haak . | |
| 3,926,521 | 12/1975 | Ginzel | 128/763 |
| 3,965,889 | 6/1976 | Sachs | 128/764 |
| 3,983,037 | 9/1976 | Lee et al. | 422/72 |
| 4,024,857 | 5/1977 | Blecher et al. | 422/102 |
| 4,091,802 | 5/1978 | Columbus | 128/764 |
| 4,136,036 | 1/1979 | Columbus . | |
| 4,225,558 | 9/1980 | Peterson et al. | 422/72 |
| 4,233,029 | 11/1980 | Columbus | 422/100 |
| 4,250,893 | 2/1981 | White . | |
| 4,269,197 | 5/1981 | Gilbard . | |
| 4,314,570 | 2/1982 | Sarstedt | 422/102 |
| 4,396,024 | 8/1983 | Sarstedt | 128/763 |
| 4,397,318 | 8/1983 | Burns | 128/767 |
| 4,411,163 | 10/1983 | White | 128/763 |
| 4,463,616 | 8/1984 | Blecher | 73/864.11 |
| 4,579,828 | 4/1986 | Ali | 422/73 |
| 4,589,421 | 5/1986 | Ullman | 128/766 |
| 4,690,153 | 9/1987 | Losada et al. | 128/763 |
| 4,707,337 | 11/1987 | Jeffs et al. . | |
| 4,805,635 | 2/1989 | Korf et al. | 128/763 |
| 4,967,763 | 11/1990 | Nugent et al. | 128/763 |

*Primary Examiner*—James C. Housel
*Assistant Examiner*—Jan M. Ludlow
*Attorney, Agent, or Firm*—Dana M. Schmidt

[57] ABSTRACT

A device and method constructed to collect a liquid into a device so that the liquid is first drawn in to an intermediate point by capillary attraction only, and then from that intermediate point further by gravity. The device features two apertured portions connected at the intermediate point so as to be angled to each other. The first portion provides the capillary attraction through its aperture by preferably oppositely disposed surfaces spaced a distance no greater than that which will maintain capillary flow into that portion through the aperture; The second portion provides gravity flow further into the device from the intermediate point by a spacing of the opposed surfaces a distance effective to allow gravity to passively overcome any surface attraction caused by the opposed surfaces, and the inclination of that portion to drop below the horizontal plane extending from the intermediate point. The aperture provided in the second portion acts as a vent and a non-sealing cover is seated over the aperture in the first portion after liquid collection to permit centrifugation and pipetting through the vent.

17 Claims, 7 Drawing Sheets

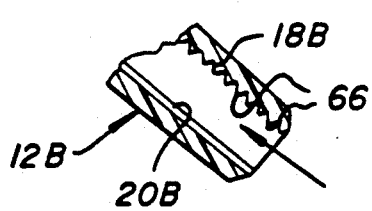
Fig. 6
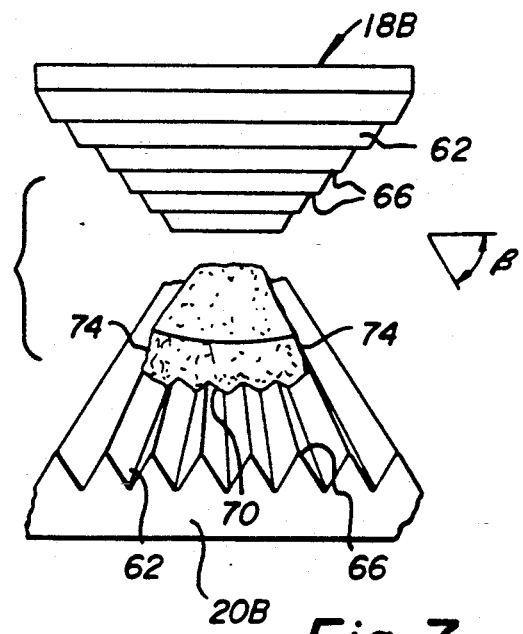
Fig. 7
Fig. 8
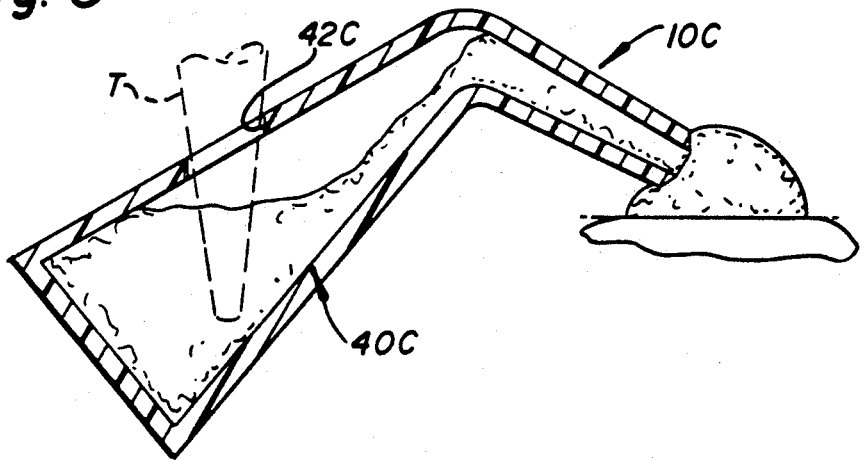
Fig. 9
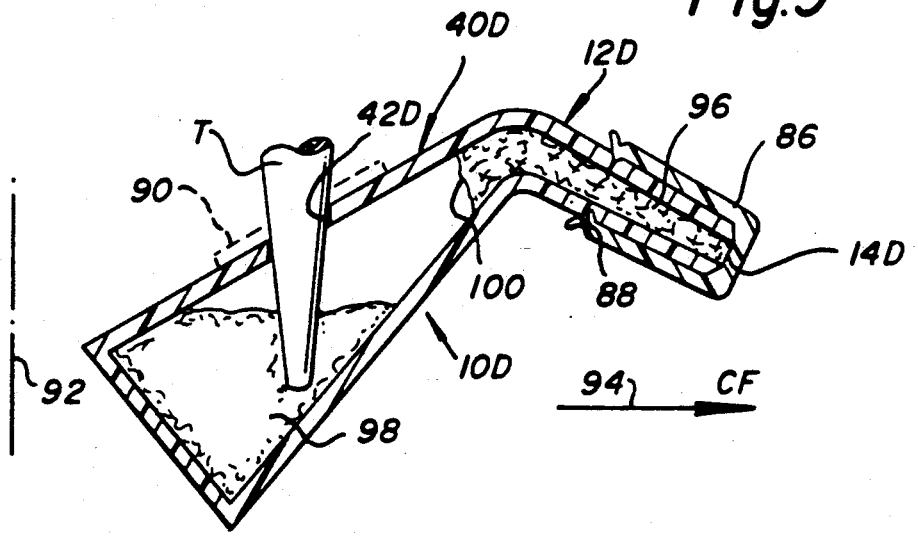

GRAVITY ASSISTED COLLECTION DEVICE

FIELD OF THE INVENTION

The invention relates to a device and method for collecting liquid from a non-pressurized source, using capillary attraction.

BACKGROUND OF THE INVENTION

In the field of capillary collection devices, attempts have been made with varying degrees of success to draw in body fluids by capillary attraction, from a source such as a finger prick, or an eyelid in the case of tear fluid. Generally, such devices rely on the capillary transport created by a capillary spacing throughout the storage volume, as shown in, e.g., U.S. Pat. Nos. 4,136,036 and 4,269,197 (FIG. 5). Once collected, the body fluid can be further processed. In the case of blood, phase separation is achieved by centrifugation and serum or plasma is collected from the device. In the case of tear fluid, the liquid is expelled under pressure.

Although such devices have functioned for their intended purpose, they have experienced a minor drawback—they are limited as to the volume that is collected. In the case of tear liquid, only 0.4 μL is needed, so this is not a problem. However, for other liquids more may be needed or desired in some cases. The use of strictly a capillary passage throughout the collection volume limits the total volume. On the other hand, if to enhance the volume the capillary spacing is increased beyond that which provides capillary attraction, then the ability to continue filling the volume becomes lost, since the capillary effect is destroyed. The two above-noted patents do not suggest a fill method to be used when such capillarity is lost.

What has been needed, therefore, prior to this invention, is a liquid collection device that can provide a capillary fill mechanism without the limitations in volume that this has required in the past.

SUMMARY OF THE INVENTION

The device that I have designed overcomes these problems by deliberately minimizing the controlling capillary effect in a portion of the collecting chamber that is angled, so that that portion is benefited by gravity More specifically, in accord with one aspect of the invention, there is provided a liquid collection device comprising means defining a chamber, an inlet aperture to the chamber, and a vent aperture out of the chamber, the chamber comprising first and second portions angled with respect to each other at a junction, with one of the apertures being in each portion. The first chamber portion includes the inlet aperture and comprises means for drawing in liquid at the inlet aperture by capillary attraction only, and the second chamber portion includes the vent aperture and comprises opposed surfaces which are all spaced apart a distance effective to allow gravity to passively overcome any surface attraction caused by the opposed surfaces, the spaced-apart surfaces of the second chamber portion being joined to the spaced-apart surfaces of the first chamber portion at the junction between the chamber portions whereby gravity can be used to assist capillary flow to fill the device.

In accord with another aspect of the invention, there is provided a liquid collection device comprising means defining a chamber, an inlet aperture to the chamber, and a vent aperture out of the chamber, the chamber comprising first and second portions angled with respect to each other at a junction, with one of the apertures being in each portion. The first chamber portion includes the inlet aperture and comprises spaced-apart surfaces of which at least two of them are spaced a distance no greater than that which provides capillary attraction of the liquid through the inlet aperture into the chamber, and the second chamber portion includes the vent aperture and comprises opposed surfaces which are all spaced apart a distance effective to allow gravity to passively overcome any surface attraction caused by said opposed surfaces, the spaced-apart surfaces of the second chamber portion being joined to the spaced-apart surfaces of the first chamber portion at the junction between the chamber portions, whereby gravity can be used to assist capillary flow to fill the device.

In accord with yet another aspect of the invention, there is provided a method of filling a collection device with liquid from a source of the liquid at atmospheric pressure only. This method comprises the steps a) drawing into an intermediate point in the collection device by capillary attraction only, some liquid from a source of the liquid at atmospheric pressure, and b) drawing in the liquid from the intermediate point further into the collection device by gravity, so that a volume can be collected as a capillary draw that is larger than the volume that is possible without the gravity assist of step b).

In accord with still another aspect of the invention, there is provided apparatus for collecting the lighter phase from phase-separated whole blood, the apparatus comprising:

a collection and separation device having sufficient chambers for partitioning most of the lighter phase from the heavier phase of the whole blood after phase separation, and a vent aperture allowing access to the location of the lighter phase, a pipette tip constructed to be inserted into the vent aperture and into the lighter phase at the vent aperture, and seal means between and surrounding the pipette tip and the aperture for sealing the tip to the device and preventing air from leaking into the vent aperture while using the tip to draw out the lighter phase.

Accordingly, it is an advantageous feature of the invention that much larger volumes of liquids can be drawn by capillary action than have been possible heretofore.

A related advantageous feature of this invention is that gravity is useful in filling the collection device of the invention without destroying the capillary attraction that is also used.

A further advantageous feature is that serum or plasma can be separated in such a device and easily removed by a pipette tip.

Other advantageous features will become apparent upon reference to the following Detailed Description when read in light of the attached drawings.

BRIEF DESCRIPTION OF THE DRAWINGS

FIG. 6 is a fragmentary section view similar to that of FIG. 1, but of another embodiment and prior to use;

FIG. 7 is an exploded perspective view looking in the direction of the arrow of FIG. 6;

FIG. 8 is an elevational view similar to that of FIG. 1, but illustrating yet another embodiment;

FIG. 9 is a view similar to that of FIG. 8, but illustrating another method of use;

FIGS. 12-15 are plan views similar to that of FIG. 10, but showing the device in its stages of use;

DESCRIPTION OF THE PREFERRED EMBODIMENTS

The invention is hereinafter described in connection with the preferred embodiments, in which the collection chamber is described as having two portions, each with certain preferred shapes to collect whole blood. In addition, the invention is also useful to collect any kind of liquid at atmospheric pressure, with more than 2 portions having widely varying shapes, provided the first portion of the chamber is effective to draw in the liquid by capillary attraction only, and the second portion of the chamber is effective to allow gravity to passively overcome any surface attraction caused by opposed surfaces of that portion. As used herein, "passively overcome" means without the need for or influence of applied forces, such as could occur by shaking the device, etc.

The terms "upstream", "downstream", "horizontal", "up" and "down" are used in this application to refer to normal location and orientations of the device during the usage that is taught herein.

Figure 1:
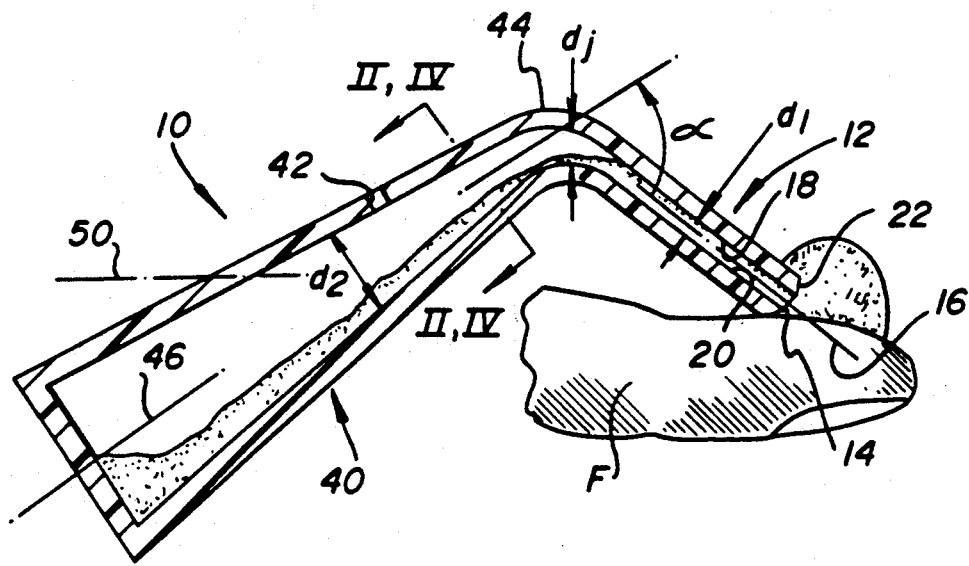
FIG. 1 is a fragmentary elevational view, partly in section, illustrating a device of the invention being used to collect blood from a finger prick.

As shown in FIG. 1, a device 10 is constructed in accordance with the invention so as to comprise a first portion 12 having an inlet aperture 14, and a second portion 40 having a vent aperture 42. The two portions are joined together at juncture 44 so as to form an angle alpha between their respective axes of symmetry 16 and 46. "Alpha" can vary from between about 60° and about 85°, the value of 80° being preferred. The value that is chosen is such as to maximize the use of gravity to collect liquid in portion 40, while facilitating collection in portion 12 while keeping finger F horizontal. That is, if alpha were much less than about 60°, then finger F would have to be tilted too far off the horizontal to still provide gravitational attraction in portion 40, and then the drop of blood would fall off the finger.

Importantly, portion 12 is defined by opposing surfaces, at least two of which (18 and 20) are spaced apart a distance $d_1$ that is no greater than that which will support capillary attraction of the whole blood into aperture 14 and portion 12. Most preferably, $d_1$ is between about 0.12 mm and about 0.3 mm. This distance $d_1$ is preferably maintained, or at the very least, is not exceeded, for the entire length of the portion 12 from aperture 14 to juncture 44. An easy construction to achieve this effect is a cylindrical tube 12', FIG. 3, having as its inside diameter, distance $d_1$.

Although portion 12 can be shaped various ways at aperture 14, a preferred configuration is one in which portion 12 is chamfered to form an annular ring 22 that forms a non-orthogonal angle with axis 16. Such annular ring provides a resting surface for portion 12 that ensures that aperture 14 will remain open to flow from the drop. Without that angled surface, there could be a tendency to rest portion 12 on the finger so as to orient axis 16 perpendicular to the finger, so that the finger accidentally seals off aperture 14 to prevent inward flow of blood.

In contrast to portion 12, portion 40 is constructed so as to overcome capillary attraction and so as to allow gravity to fill portion 40. Capillary attraction within portion 40 is undesirable, since such attraction can override the effect of gravity. Hence, no more than a very weak capillary effect is tolerated in portion 40.

Accordingly, the distance $d_j$ between surfaces 18 and 20 at junction 44 is the maximum distance for $d_1$ that can provide capillary draw up to juncture 44, and thereafter, that distance increases to distance $d_2$ to allow gravity to overcome capillary flow from juncture 44 into portion 40. As a result, because of the angle alpha and the tilting of axis 46 down below horizontal, gravity is the attractive force of liquid into portion 40 from juncture 44. Most preferably, $d_j$ is about 0.2 mm for blood, but this can vary for other liquids.

Most preferably, juncture 44 and the opposing surfaces of portion 40 are characterized by a gradual increase in spacing between the surfaces, to avoid creating abrupt steps or ledges that can block liquid flow, either into or out of the device. Accordingly, it is preferred that distance $d_2$ have a gradual increase in value as portion 40 extends away from juncture 44, rather than abrupt change which could create an edge effect that could interfere with the automatic influx of liquid into portion 40, provided by the capillary attraction of portion 12. Similarly, no abrupt steps are desired in opposed surfaces of portion 40, lest they hamper the emptying of that portion when device 10 is inverted for the emptying step.

Figure 2:
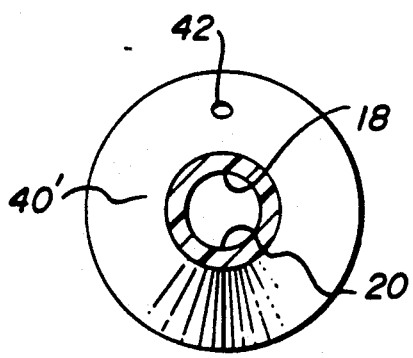
FIG. 2 is a section view taken generally along the line II—II of FIG. 1 and showing a first embodiment of the invention.
Figure 3:
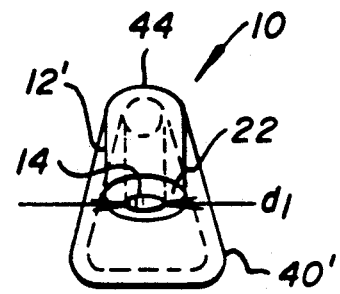
FIG. 3 is a front elevational view of the embodiment of FIG. 2.

A convenient configuration of portion 42, if portion 12 is cylindrical, is one of a hollow cone 40', of uniform wall thickness, FIG. 2, so that surfaces 18 and 20 continue to be two parts of a continuous surface, as they were in portion 12', FIG. 3. That is, surfaces 18 and 20 provide in transverse cross-section, a circular shape throughout portions 12 and 40, in this embodiment.

Vent 42, FIGS. 1 and 2, is located anywhere in portion 40 that will a) maximize the volume that can be collected and b) allow subsequent dispensing by inverting the device and letting liquid drip out of aperture 14. Because the last bit to be expelled can require some external pressure to be applied at aperture 42, that aperture, FIG. 1, needs to be far enough away from juncture 44 to ensure that, when device 10 is inverted, the liquid is not exposed at aperture 42. However, it should not be so far from juncture 44 as to unduly limit the volume that can be collected. Thus, some location between that actually shown and back to the horizontal line 50, is preferred.

Useful examples of the embodiment of FIGS. 1-3 will provide collectible volumes of from about 20 uL to about 150 uL of whole blood. Larger volumes are also useful, but filling times become longer and less desirable.

It is not necessary that the transverse cross-sectional shapes formed by surfaces 18 and 20 be circular. Other shapes are useful and provide even more volume, FIGS. 4 and 5. Parts similar to those previously described bear the same reference numerals to which the distinguishing suffix A has been appended.

Figure 4:
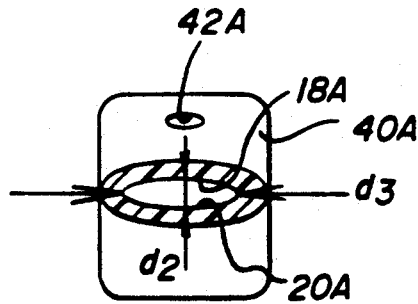
FIG. 4 is a section view taken along the line IV—IV of FIG. 1, similar to that of FIG. 2 but illustrating another embodiment of the invention.
Figure 5:
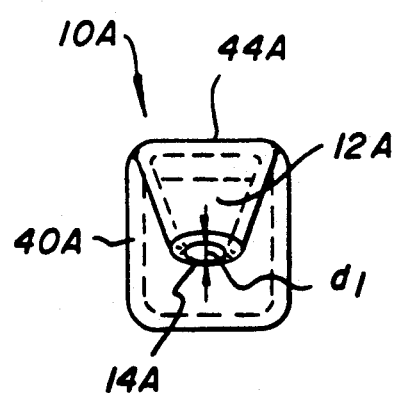
FIG. 5 is a front elevational view similar to that of FIG. 3, but of the embodiment of FIG. 4.

Thus, FIG. 5, portion 12A of device 10A has an inlet aperture 14A that is circular, and joins at juncture 44A second portion 40A that has a vent aperture 42A, FIG. 4, as described above. Furthermore, surfaces 18A and 20A are spaced a distance $d_1$, FIG. 5, that allows capillary attraction of the liquid in portion 12A, but in portion 40A they are spaced a distance $d_2$, FIG. 4, that allows gravity to overcome capillary effects, also as described above. In other words, the overall functioning of device 10A is exactly as described for the previous embodiment.

However, to collect even more volume, preferably the transverse cross-sectional shape formed by the opposing internal surfaces of portions 12A and 40A (e.g., surfaces 18A and 20A) is one that is generally elliptical, with a second spacing distance $d_3$, FIG. 4, that greatly exceeds $d_1$ (except at aperture 14A where $d_3$ is about equal to $d_1$). This applies even in portion 12A (except at aperture 14A as noted), so that such portion has a general wedge shape.

In the aforedescribed embodiments, a variety of materials is useful to form surfaces 18, 20 or 18A, 20A. Preferably, they are materials which are readily wetted by the liquid being collected. In the case of whole blood, most preferably, they are surfaces comprising glass, plastic such as nylon, polyacrylonitrile, polyesters such as poly(ethylene terephthalate), cellulose acetate, or acrylate polymers, or non-wettable surfaces further coated with a wettable material such as poly(ethylene-co-2, 2'-oxydiethylene (63/67) terephthalate), or other adhesives as described in U.S. Pat. No. 4,957,582. These adhesives can also be used to assemble the device by bonding together two halves. Surfaces 18, 20, 18A or 20A as shown are most preferably smooth surfaces, that is, given no deliberate surface features other than random irregularities not deliberately formed.

Alternatively, opposed surfaces of the first portion that provide the capillary draw can be provided with deliberate features for controlling the liquid meniscus shape and direction of advance in that first portion, FIGS. 6 and 7. Parts similar to those previously described bear the same reference numeral, to which the distinguishing suffix "B" is applied.

Thus, portion 12B of device 10B has, on opposing surfaces 18B and 20B, alternating and parallel grooves and ridges 62 and 66, respectively, FIG. 7. The grooves and ridges of surface 18B are preferably misaligned with those of surface 20B. More precisely, the grooves and ridges of one surface extend everywhere at an angle beta to the grooves and ridges directly opposite them on the other surface. Hence, a convenient configuration of the grooves and ridges is a linear one, although others are also possible to provide an angle beta of misalignment.

The purpose, as described in commonly-owned U.S. Pat. No. 4,233,029, is to ensure that the menisci 70 and 74 advancing from aperture 14B will take the shape of the ridges. Other details and possibilities of the grooves and ridges can be found in that patent.

The edge effects provided by the grooves and ridges of 18B are considered to have a negligible effect on the emptying of liquid from portion 12B when the device is inverted. The reason is that the last bit of the collected liquid is expelled from capillary portion 12B by external pressure applied at the vent aperture anyway, and this pressure will override the edge effects of the grooves and ridges.

Alternatively (not shown), the device of FIG. 6 can be modified so that the grooves on surface 20B are eliminated, leaving only the grooves on surface 18B to control the meniscus shape and advance.

As shown in FIG. 8, vent aperture 42C can be large enough to allow access of a pipette tip T to portion 40C, whereby the collected liquid can be removed by aspiration through aperture 42C.

Still further, FIG. 9, it is possible to use this device to not only collect whole blood, but also to separate serum or plasma from blood cells within the device and remove only the serum or plasma. Parts similar to those previously described bear the same reference numerals to which the distinguishing suffix "D" has been appended.

Thus, device 10D is constructed as the device in the embodiment of FIG. 8. This device also has two portions 12D and 40D, which can be configured either as shown in FIG. 3 or 5. The vent aperture 42D is shaped and positioned to allow a pipette tip to be inserted to withdraw the liquid. However, prior to this, and after the initial collection, aperture 42D is temporarily sealed with a conventional tape 90, shown in phantom. Aperture 14D is sealed with a cover 86 that is secured at 88. Device 10D is then spun about an axis 92, creating a centrifugal force CF, arrow 94, which is effective to cause phase separation of the whole blood into the heavier cell fraction 96, and a lighter serum or plasma fraction 98 adjoining, during spinning, cell fraction 96 at interface 100. When spinning ceases, the lighter fraction falls to the position shown in solid lines.

To retain the cellular fraction in place, as shown, device 10D preferably has preincorporated into it a polymeric amine coagulator, preferably in liquid or solution Examples are described in commonly owned, U.S. Pat. No. 4,994,192 by Corin et al, entitled "Amine Polymers As Coagulator Accelerators in Blood Phase Separation". The contents of that application are expressly incorporated herein by reference. Highly preferred examples include polylysine at a weight average molecular weight of about 77,000 Daltons, at a concentration of 0.486 mg/mL, and poly(2-aminoethyl methacrylate hydrochloride) having a weight average molecular weight of about 250,000 PVP equivalents at a concentration of 0.92 mg/mL. These coagulators are effective to bind the cellular fraction 96 to itself so that it remains in place, even if device 10D is shaken vigorously in the orientation shown.

Still further, after all of the lighter fraction 98 is aspirated out, the heavier fraction 96 is also optionally removable. Cover 86 is removed, and a source of external air pressure (not shown) is applied to vent 42D while device 10D is reoriented with portion 12D pointed downward. Such pressure can then gently push the coagulated cells out of aperture 14D into another container (not shown) for further processing, such as the extraction of DNA for PCR amplification and detection, using, e.g., the devices taught in commonly owned EPA 381501. Conventional processes can be used for the extraction steps, followed by the aforesaid amplification and detection of targeted DNA.

Alternatively, the upper wall surface of the device, shown as having the vent aperture therein, can be sufficiently flexible as to allow the contents of the device to be forcibly expelled out of the inlet aperture simply by manually pressing down that upper wall surface.

It is not necessary that phase separation occur by centrifuging only in the direction 94 shown in FIG. 9. The opposite direction can be used, as shown in FIGS. 11-15 in particular. Parts similar to those previously described bear the same reference numeral, to which the distinguishing suffix "E" is appended.

Figure 10:
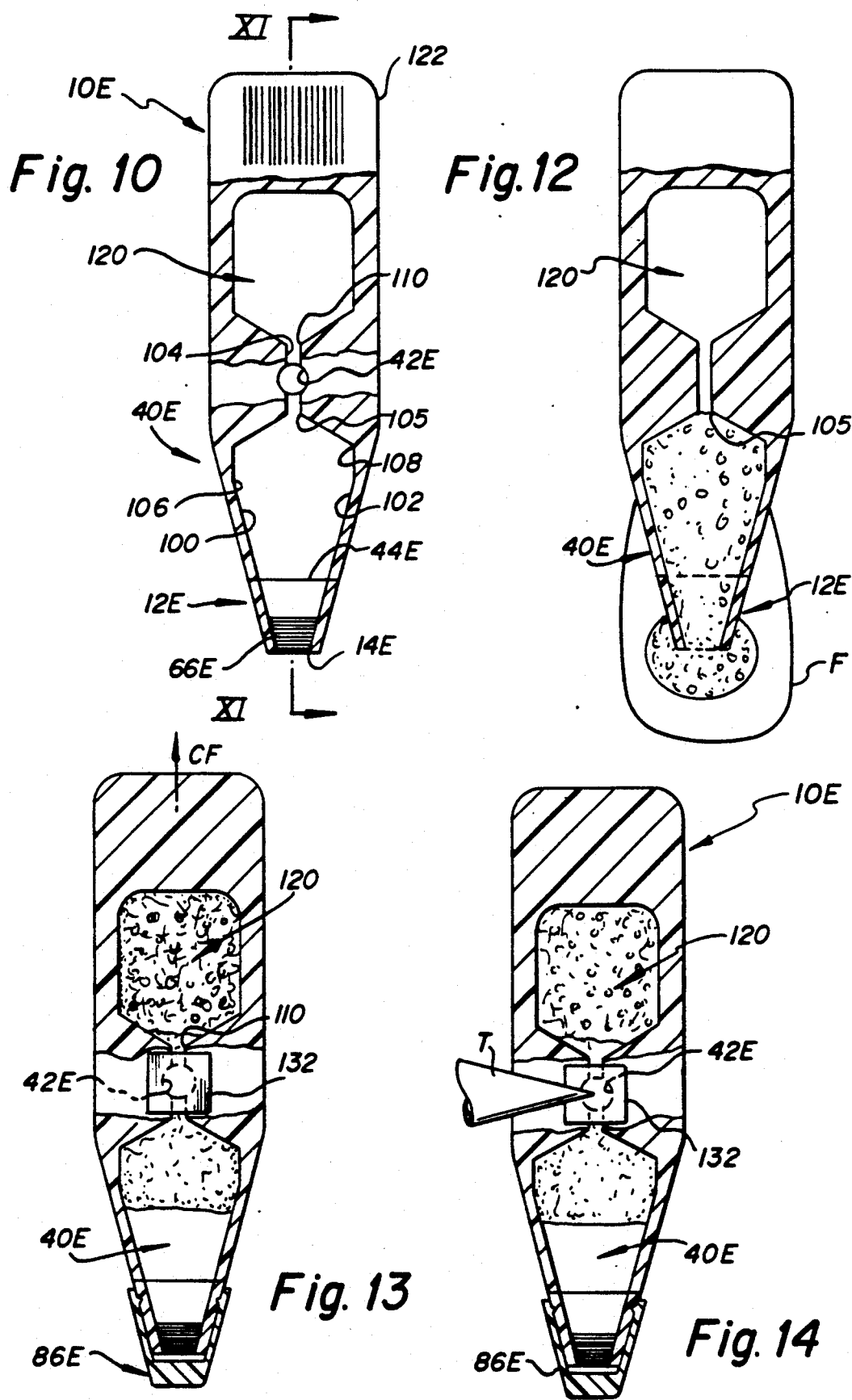
FIG. 10 is a partially sectioned plan view illustrating yet another embodiment of the invention.
Figure 11:
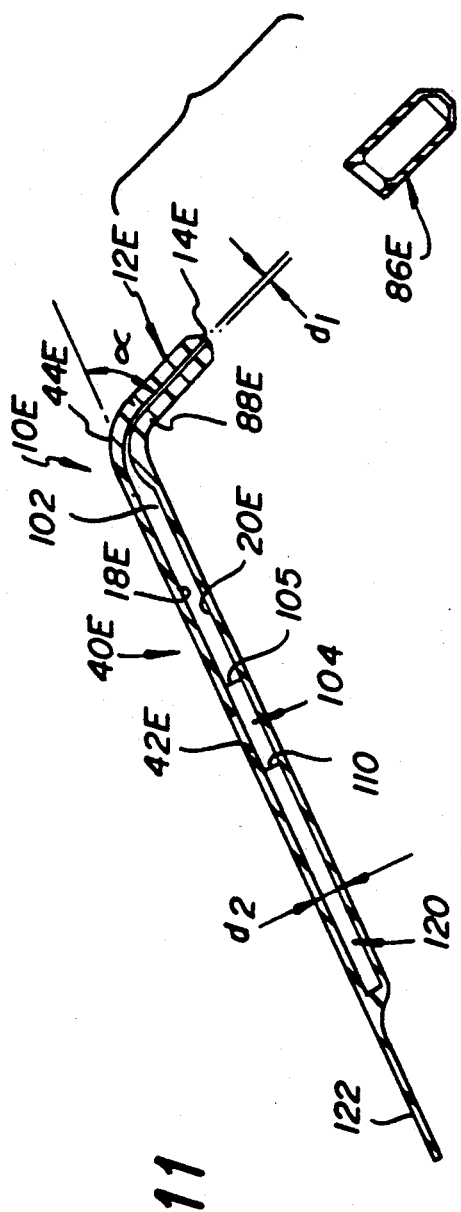
FIG. 11 is a section view taken generally along the line XI—XI of FIG. 10.

Thus, FIGS. 10 and 11, device 10E comprises a device very similar to that of FIG. 8 in that a first chamber portion 12E is provided with a capillary spacing $d_1$, FIG. 11, and a second chamber portion 40E joined to and angled with respect to portion 12E at junction 44E. The spacing apart of opposed surfaces 18E and 20E in chamber portion 40E is at least by a distance $d_2$ at which gravity will passively overcome any capillary attraction between surfaces 18E and 20E. Inlet aperture 14E occurs in chamber portion 12E and vent aperture 42E in chamber portion 40E, and grooves 62E are optionally provided, FIG. 10, in surface 18E in chamber portion 12E.

However in this embodiment, two opposing surfaces of second chamber portion 40E are constructed together to provide an automatic stop to the flow of liquid under gravity. For example, side wall surfaces 100 and 102 are so constructed, FIG. 10, to form a narrow neck passageway 104 that starts at location 105. However, passageway 104 is sufficiently wide as to allow free flow therethrough of the heavier phase (blood cells). Most preferably, all corners 106, 108 other than the corner at 105, that necessarily occur in chamber portion 40E upstream of location 105, are formed so as to have an interior angle larger than 90°, to ensure that blood flow will continue, under gravity, up to location 105.

Neck passageway 104 continues past the location of aperture 42E, to a location 110, where side wall surfaces 100 and 102 are spaced farther apart to create a blood-cell collection chamber 120, as will become apparent. A handle 122 can be further attached downstream of chamber 120, with suitable markings such as a bar code, etc.

This embodiment also uses a cover 86E, FIG. 11, as in the previous embodiment, that seats via its ribs that enter grooves 88E. However, when so seated, inlet aperture 14E is covered but not sealed, so that air flow still occurs into aperture 14E.

In use, device 10E is positioned similarly to device 10C, FIG. 8, so that, FIG. 12, a drop of whole blood is drawn into portion 12E by capillary attraction, and then into portion 40E by gravity, up to, but not beyond, location 105. For convenience, a suitable mark 130 can be placed between locations 105 and 110, and the walls of device 10E can be transparent, to assist the user in determining when liquid has filled up to location 105.

Thereafter, FIG. 13, vent aperture 42E is sealed over with an adhesive foil 132, and cover 86E placed onto the device. A centrifugal force CF is applied, arrow CF, to provide phase separation. This time, however, the heavier material (blood cells) is collected only in collection chamber 120, and the lighter phase (serum or plasma) is collected in the portion of chamber portion 40E that brackets aperture 42E (as well as locations 105 and 110).

To ensure that the lighter phase will in fact extend beyond location 110, chamber 120 is preferably constructed so that it provides a collection volume that is greater than the volume of cells that can be expected, from any hematocrit value, given a predetermined volume of whole blood collected in both portion 12E and that part of chamber portion 40E that is upstream from location 105. For example, if the volume collected in portion 12E is about 10 uL, and the volume collected in portion 40E upstream of location 105 is about 50 uL, then the volume of chamber 120 should be at least about 36 uL to be sure that enough of the lighter phase brackets the aperture 42E during this step. Stated another way, the volume of portion 40E downstream of location 105 should be at least about 60% of the total volume of portions 12E and 40E.

Figure 20:
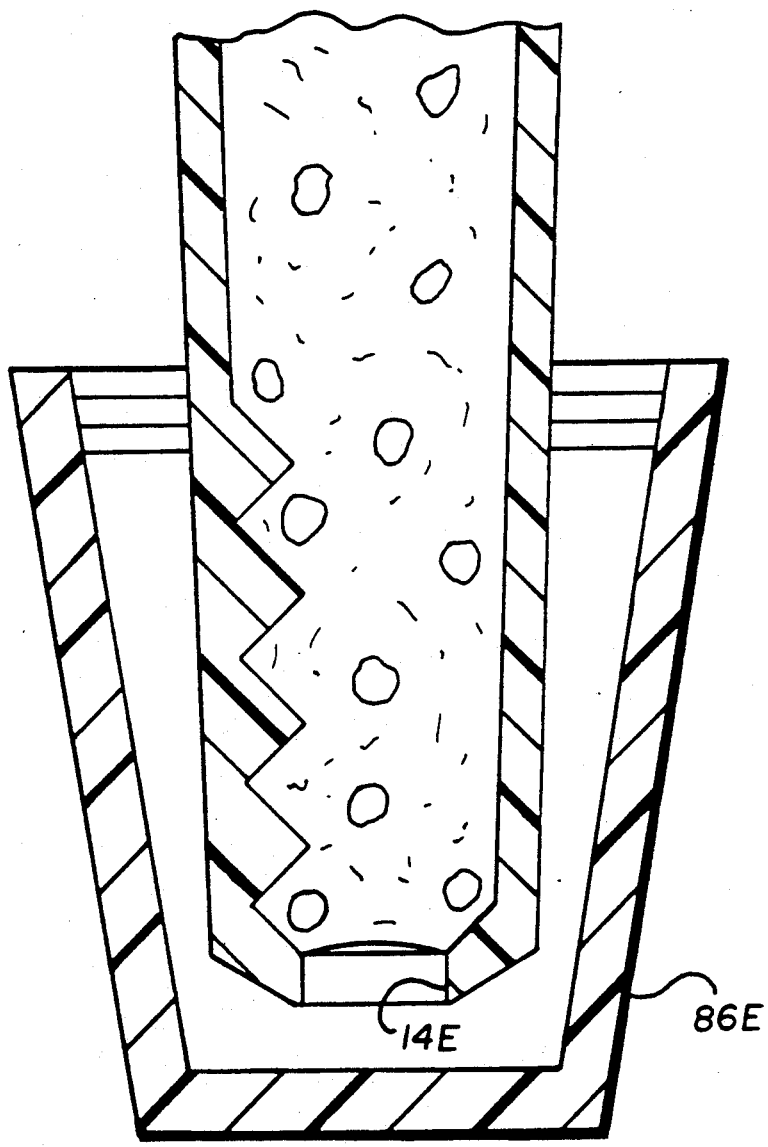
FIG. 20 is a fragmentary section view taken generally along the line XX—XX of FIG. 19.

Following phase separation, FIG. 14, a pipette tip T is used to penetrate foil 132. Thereafter, a source of vacuum is applied to tip T and the lighter phase is drawn out. Because vent 14E is unsealed by cover 86E, FIG. 20, the lighter phase recedes as shown by arrow 140, FIG. 15, leaving undisturbed the liquid material (heavier and lighter phases) that is located between location 110 and handle 122.

Figure 16:
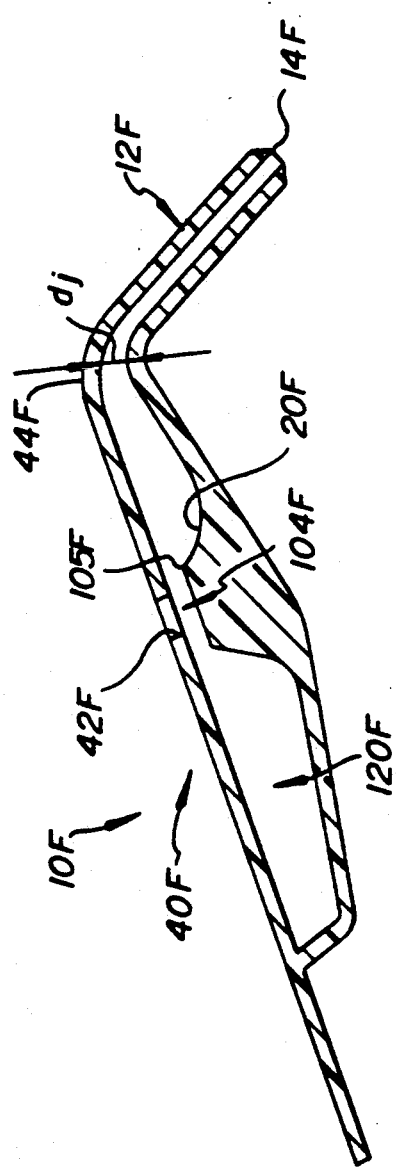
FIG. 16 is a side elevational view in section similar to that of FIG. 1, but of still another embodiment.
Figure 15:
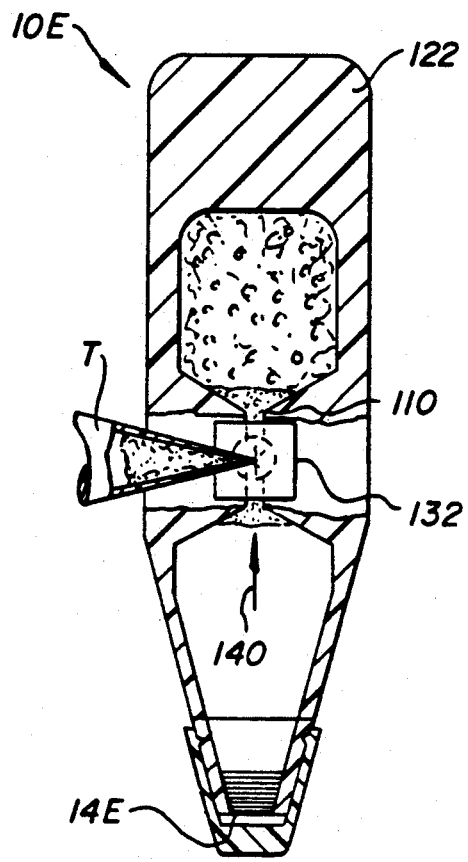

The construction forming passageway 104 need not be provided by side walls of the second chamber portion. Instead, it can be formed by one or both of the other opposing surfaces, as shown in FIG. 16. Parts similar to those previously described bear the same reference numerals, to which the distinguishing suffix "F" has been appended. Thus, device 10F comprises first chamber portion 12F joined to second chamber portion 40F at junction 44F, with an inlet aperture 14F, a vent aperture 42F and a spacing distance $d_j$ at junction 44F, as described for FIG. 11. Neck passageway 104F is also formed to extend past aperture 42F. However, the construction that provides passageway 104F is formed by extending one (as shown) or both wall surfaces 20F (or also 18f, not shown). Thus, incoming whole blood stops flowing when it reaches the sharp edge provided by location 105F.

Figure 17:
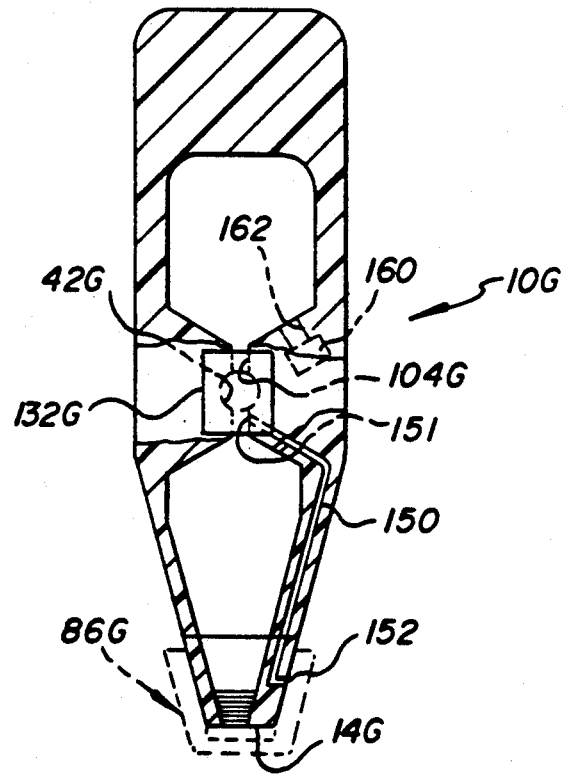
FIG. 17 is a plan view similar to that of FIG. 10, but of yet another embodiment.

In the utilization process described in connection with FIGS. 10-15, it is not necessary that aperture 42E be sealed in the middle of the process. Rather, it can be pre-sealed, as shown in FIG. 17, provided a supplemental vent is provided. Parts similar to those previously described bear the same reference numeral, to which the distinguishing suffix "G" is appended. Thus, FIG. 17, device 10G is substantially identical to that of FIG. 10, except that, as manufactured, seal 132G is in place. Air that would otherwise be trapped as liquid is drawn into inlet aperture 14G, now is vented by an auxiliary vent passageway 150 extending from an opening 151 in passageway 104 adjacent to aperture 42G, through a wall of device 10g to an auxiliary vent orifice 152 located adjacent to aperture 14G. Orifice 152 is positioned so that it, but not aperture 14G, is sealed when cover 86G, shown in phantom, is seated in place. Thus, when vent aperture 42G is penetrated by a pipette tip, the only flow of air that is possible is through inlet aperture 14G, allowing the lighter phase, following phase separation, to be withdrawn.

Yet an additional option, also shown in phantom, FIG. 17, is to provide a supplemental chamber 160 connected via a passageway 162 to the collection chamber 120G, in which is contained the polymeric coagulator material described above.

Figure 18:
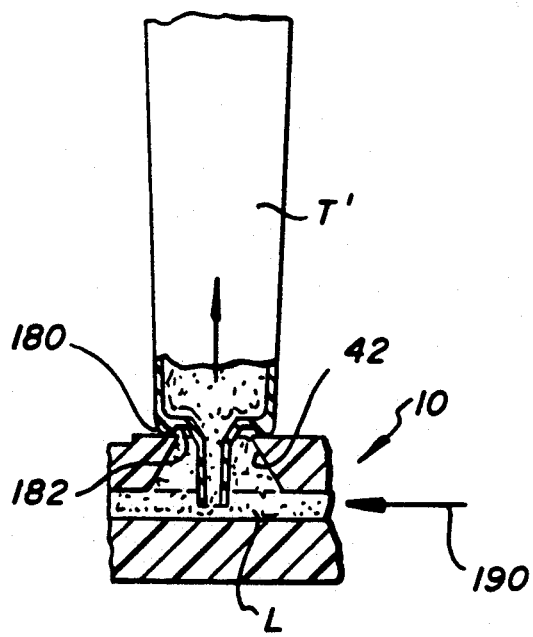
FIG. 18 is a fragmentary elevational view in section showing another aspect of the invention involved during liquid removal.

For maximum collection of liquid via pipette tip T, in the embodiments of FIGS. 10-17, it is preferred that the tip be sealed against the device so that, as already indicated, the only access of air into the device is via the inlet aperture. Such an arrangement is illustrated in FIG. 18. Thus, device 10 (which can be any of the previous embodiments) is used with a pipette tip T so that an elastic sealing ring 180 surrounds and is between said tip and the vent aperture 42 (which can be any of the previously described vent apertures.) As shown, ring 180 is an elastomeric ring integral with and projecting from a surface 182 on tip T'. Alternatively (not shown), ring 180 can be located on or provided by exterior surface 184 of device 10. In this fashion, the only manner in which air can flow into device 10 is via the inlet aperture, not shown but indicated via arrow 190, thus ensuring that most of the lighter phase 2 will be collected by tip T'.

Except as described above, the pipette tip can be any conventional tip used with any conventional pipette or aspirating device.

Aspiration of the lighter phase from the device of this invention can be done manually, or automatically by machine.

Figure 19:
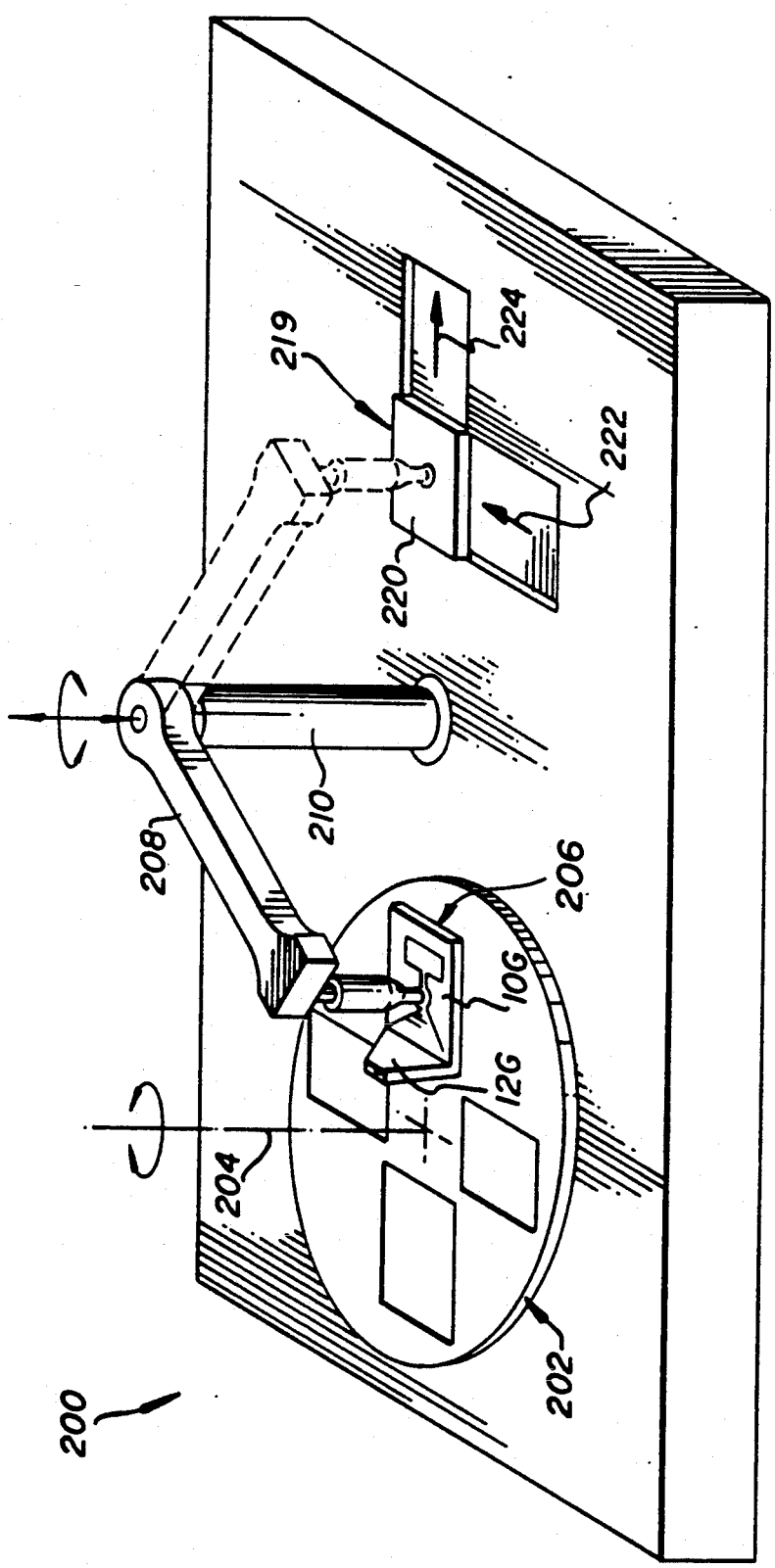
FIG. 19 is a perspective view of apparatus used in conjunction with the apparatus of FIG. 18.

A preferred automated process is shown in FIG. 19. The preferred form of the liquid collection device, for such apparatus, is that of FIG. 17, i.e., device 10G, except that the vent aperture is located in the underneath of the device rather than the upper surface. Since the vent aperture is always sealed in that embodiment, except upon tip penetration, the under surface is just as suitable as the upper surface.

The automated apparatus 200 preferably comprises a centrifuge rotor 202 mounted to rotate about axis 204 and driven by conventional motor means, not shown. Suitable clamps, not shown, hold a collection device 10G in place, of which only one is shown, at the aspirating station 206. Tips T' of the type shown in FIG. 18 are mounted onto aspirator arm 208, that is pivotally mounted on rod 210 constructed to move up and down also, on command, by a drive mechanism (not shown). Within rod 210, not shown, is a passageway that connects with the interior of tip T' and with a conventional metering pump. Such pump is effective to first generate a partial vacuum within tip T', and then a partial pressure when the tip is rotated (shown in phantom) to station 212 for dispensing the liquid onto or into any suitable container 220. Container 220 is automatically advanced arrow, 222, to station 212, and removed, arrow 224, by conventional pusher blades, not shown.

The invention has been described in detail with particular reference to certain preferred embodiments thereof, but it will be understood that variations and modifications can be effected within the spirit and scope of the invention.

What is claimed is:

1. A liquid collection device comprising means defining a chamber, an inlet aperture to said chamber, and a vent aperture out of said chamber, said chamber comprising first and second portions angled with respect to each other at a junction, with one of said apertures being in each portion, said first chamber portion including said inlet aperture and comprising means for drawing in liquid at said inlet aperture by capillary attraction only, and said second chamber portion including said vent aperture and comprising opposed surfaces which are all spaced apart a distance effective to allow gravity to passively overcome any surface attraction caused by said opposed surfaces, said opposed surfaces of said second chamber portion being joined to said opposed surface of said first chamber portion at said junction between said chamber portions.

whereby gravity can be used to assist capillary flow to fill said device, and further including a cover for said inlet aperture and means for removably seating said cover over said inlet aperture, said cover and said seating means being constructed to provide air access from the exterior of said cover to said inlet aperture so that said inlet aperture is covered but not sealed when said cover is seated whereby when said cover is seated over said inlet aperture, liquid collected in the second portion can be pipetted through the vent aperture.

2. A liquid collection device comprising means defining a chamber, an inlet aperture to said chamber, and a vent aperture out of said chamber, said chamber comprising first and second portions angled with respect to each other at a junction, with one of said apertures being in each portion, said first chamber portion including said inlet aperture and comprising spaced-apart surfaces of which at least two of them are spaced a first pre-determined distance no greater than that which provides capillary attraction of the liquid through said inlet aperture into said chamber, and said second chamber portion including said vent aperture and comprising opposed surfaces which are all spaced apart a second pre-determined distance effective to allow gravity to passively overcome any surface attraction caused by said opposed surfaces, said opposed surfaces of said second chamber portion being joined to said opposed surfaces of said first chamber portion at said junction between said chamber portions, whereby gravity can be used to assist capillary flow to fill said device, and further including a cover for said inlet aperture and means for removably seating said cover over said inlet aperture, said cover and said seating means being constructed to provide air access from the exterior of said cover to said inlet aperture so that said inlet aperture is covered but not sealed when said cover is seated whereby when said cover is seated over said inlet aperture, liquid collected in the second portion can be pipetted through the vent aperture.

3. A device as defined in claim 2, wherein said first chamber portion comprises a cylindrical tube with an internal diameter that does not exceed said first distance providing capillary attraction, and said second chamber portion comprises a conical tube.

4. A device as defined in claim 2, wherein said first distance of said first chamber portion is no greater than about 0.3 mm and said second distance of said second chamber is no less than about 0.3 mm.

5. A device as defined in claim 4, wherein said first distance of said first chamber portion is between about 0.08 mm and about 0.3 mm.

6. A device as defined in claim 4, wherein said second distance of said second chamber portion is about 0.2 mm at said junction between said portions and increases gradually in spacing as said second chamber portion surfaces extend away from the angle between said chamber portions.

7. A device as defined in claim 1 and 2, and further including means in said first chamber portion for controlling the liquid meniscus shape and direction of advance in said first chamber portion.

8. A device as defined in claim 1 or 2, wherein said inlet aperture is circular in cross-sectional shape, and said first chamber portion extends from said inlet aperture with generally a wedge-shape.

9. A device as defined in claim 1 or 2, and further including an auxiliary vent passageway extending from an orifice adjacent to said vent passageway in a wall of said device to an auxiliary vent orifice adjacent to said inlet aperture, and wherein said cover when seated seals off said auxiliary orifice.

10. A device as defined in claim 1 or 2, and further including an auxiliary vent passageway extending from an orifice adjacent to said vent passageway in a wall of said device to an auxiliary vent orifice adjacent to said inlet aperture.

11. A device as defined in claim 1 or 2, and further including a supplemental chamber portion containing a coagulator for blood cells, said supplemental chamber portion being connected to said second chamber portion by a passageway.

12. A device as defined in claim 1 or 2, wherein at least one of said spaced-apart surfaces of said second chamber portion is sufficiently flexible as to allow manual depression of said one surface to forcibly eject any liquid contained in said second 13. A device as defined in claim 1 or 2, and further including means for sealing a pipette tip to said vent aperture for removal of liquid without air leakage into the liquid.

14. A device as defined in claim 1 or 2, wherein two of said opposed surfaces are constricted together at a predetermined location in said second chamber portion by an amount and with a shape sufficient to halt flow of liquid past said constricted location by gravity, the spacing of said surfaces at said constricted location being sufficiently large however as to allow flow of liquid therepast upon the influence of centrifugal force.

15. A device as defined in claim 14, wherein said vent aperture is located in said second chamber portion downstream from said constriction location.

16. A device as defined in claim 14, wherein said second chamber has a selected volume, and said vent aperture and said constricted location are predeterminedly located, such that when a predetermined amount of whole blood is drawn into said device up to said constricted location, it can be phase separated by centrifuging with said vent aperture occupying a position providing access to the lighter phase of the separated blood to permit aspiration.

17. A device as defined in claim 14, wherein a portion of one of said opposed surfaces located downstream from said constricted location during liquid flow in the device is sufficiently flexible as to be manually depressible to forcibly eject any liquid upstream of said constricted location.

* * * * *

UNITED STATES PATENT AND TRADEMARK OFFICE
CERTIFICATE OF CORRECTION

PATENT NO. : 5,230,864
DATED : July 27, 1993
INVENTOR(S) : Richard L. Coloumbus

It is certified that error appears in the above-indentified patent and that said Letters Patent is hereby corrected as shown below:

Column 9, Line 66
    Delete "chamber." and insert --chamber,--

Column 10, Line 13
    Delete "portions." and insert --portions,--

Signed and Sealed this

Fourth Day of October, 1994

Attest:

Attesting Officer

BRUCE LEHMAN

Commissioner of Patents and Trademarks